United States Patent

Harrold et al.

(10) Patent No.: US 6,512,379 B2
(45) Date of Patent: Jan. 28, 2003

(54) CONDITION MONITORING OF TURBINE BLADES AND VANES IN SERVICE

(75) Inventors: Ronald Thomas Harrold, Murrysville, PA (US); Zal N. Sanjana, Pittsburgh, PA (US)

(73) Assignee: Siemens Westinghouse Power Corporation, Orlando, FL (US)

( * ) Notice: Subject to any disclaimer, the term of this patent is extended or adjusted under 35 U.S.C. 154(b) by 5 days.

(21) Appl. No.: 09/776,864

(22) Filed: Feb. 5, 2001

(65) Prior Publication Data

US 2002/0190721 A1 Dec. 19, 2002

(51) Int. Cl.$^7$ ............................................. G01R 27/04
(52) U.S. Cl. ......................................... 324/632; 73/588
(58) Field of Search ........................ 73/577, 583, 588; 324/632, 642

(56) References Cited

U.S. PATENT DOCUMENTS

| | | | | |
|---|---|---|---|---|
| 5,170,666 A | * | 12/1992 | Larsen | ........................ 73/571 |
| 5,552,711 A | | 9/1996 | Deegan et al. | |
| 5,970,393 A | | 10/1999 | Khorrami et al. | |
| 6,057,628 A | | 5/2000 | Viljoen et al. | |
| 6,172,510 B1 | * | 1/2001 | Liu | ............................ 324/632 |

OTHER PUBLICATIONS

R.T. Harrold, "A Piezoelectric Effect in High Voltage Power Capacitors", 1983 Annual Report IEEE, pp. 68–80.

Bruce McKee et al., "Resonant Crackwires for In Situ Monitoring of Jet Engines", Jun. 2000, NASA Technical Briefs.

J.M., "General Dynamics to develop sensors for naval aircraft engines", Jul. 2000, Military and Aerospace Electronics.

W.D. Kingery et al., "Introduction to Ceramics", 2nd Ed. 1975, pp. 922–923 and 964–967.

* cited by examiner

Primary Examiner—Christine K. Oda

(57) ABSTRACT

A method and apparatus for monitoring the condition of a thermal barrier coating on the vanes and blades of a combustion turbine relies on a piezoelectric or electrostrictive effect, or tribo-charging generated within the coating. Gas flowing through the turbine will apply pressure to the vanes and blades, resulting in a strain on the blades and vanes, and causing friction as it passes the vanes and blades. An electric current is generated between the coating and vane or blade, either by a pressure-induced piezoelectric effect, a strain-induced electrostrictive effect, or friction-induced tribo-charging. This current causes a radio frequency signal, which can be detected by a high temperature antenna as the blade passes the antenna. One blade may be intentionally designed to produce a signal different from the remaining blades, thereby becoming a marking blade. After amplification and filtering, the radio signals may be analyzed and stored. Changes in the signals produced may indicate a deterioration of the coating. Counting the number of signals from the marking blade can determine the specific blade or vane requiring service.

31 Claims, 3 Drawing Sheets

CONDITION MONITORING OF TURBINE BLADES AND VANES IN SERVICE

BACKGROUND OF THE INVENTION

1. Field of the Invention

The invention generally relates to an apparatus and method of monitoring radio frequency signals generated by piezoelectric effects, electrostrictive effects, or tribo-charging. More specifically, the invention relates to an apparatus and method of online monitoring for defective components within a combustion turbine.

2. Description of the Related Art

Combustion turbines typically operate at extremely high temperatures, for example, 2500° F. to 2900° F. (1371° C. to 1593° C). Such high temperatures can cause failure of various components unless they are protected from the heat. These components include the rotating blades of the turbine, and the vanes for directing gas flow within the turbine. A typical combustion turbine will have three to four rows each of blades and vanes, with approximately 50 to 100 blades or vanes per row, and will typically have approximately 500 total blades and vanes to protect. A commonly used material for vanes and blades is nickel-cobalt. These components are generally insulated by a thermal barrier coating so that the turbine can be operated at such high temperatures without causing excessive deterioration of these components. A typical thermal barrier coating is yttria-zirconia.

Currently, it is necessary to periodically stop the turbine and inspect the components for deterioration of the thermal barrier coating, defects in other coatings, or other defects, for example, formation of cracks in the underlying components. It would be desirable to monitor the condition of these components while the turbine is in use. Avoiding the need to periodically stop the turbine for inspection reduces downtime, increasing the turbine's efficiency. Likewise, early detection of defects reduces repair costs and outage time, again increasing turbine efficiency. Although other systems of monitoring the condition of turbines during use have been proposed, the present invention provides the unique advantage of providing early detection of defects, and a means of locating the defect; simplifying the inspection and repair procedure once a defect is identified.

One proposed monitoring system is described in U.S. Pat. No. 5,552,711 issued to T. Deegan et al. on Sep. 3, 1996. This patent describes the monitoring of the condition of a structured surface by mounting microstrip antennas on the surface. The antennas comprise a dielectric substrate having a metallic patch on one side and completely plated by a conductor on the other side. The antennas may be integrated onto dielectric-piezoelectric substrates. The antennas receive power through electromagnetic radiation, possibly radio frequency waves. This power can be used to actuate the piezoelectric material. Signals from the piezoelectric material can be communicated through the microstrip antennas, thereby providing feedback regarding the condition of the surface. Uses for such a monitoring system include the monitoring of turbine blades. This system, however, requires the antennas to rotate with the turbine blades, thereby subjecting the antennas to additional stress.

Another proposed system for monitoring the condition of turbine blades is described in U.S. Pat. No. 5,970,393 issued to K. Khorrami et al. on Oct. 19, 1999. This system relies on the measurement of electromagnetic emissions of ions emitted by portions of the blade which are deteriorating. This system does not include a means for locating the stage wherein the failed component is located.

Accordingly, there is a need to provide an online monitor for the condition of combustion turbine components wherein the components of the monitor are supported by stationary portions of the turbine. Additionally, there is a need to identify the stage wherein a defect in the vanes and blades of a combustion turbine is forming. Further, there is a need to identify the location of the defective component, thereby simplifying and speeding the repair process.

SUMMARY OF THE INVENTION

The preferred embodiment of the invention is a method and apparatus for monitoring the condition of a component within a combustion turbine during operation of the turbine, such as the thermal barrier coating on the vanes and blades within the turbine. The principal embodiment of the system relies on detecting changes in the levels of the radio frequency signals generated by a piezoelectric effect or electrostrictive effect created between the coating and the substrate by gas pressure exerted on the vanes and blades, or from tribo-charging due to friction between the gas and the coating.

As the combustion turbine is operated, gas pressure flowing past the vanes and pushing against the blades will apply pressure to these components, causing an electric current resulting from a piezoelectric effect between the thermal barrier coating and the component. Although most materials producing a piezoelectric effect have been previously polarized by heating the material to a high temperature and passing DC current through the material, the present inventors have found that thermal barrier coatings exhibit a piezoelectric effect due to the polarity of molecular impurities within the coating. This current will cause the blade or vane to radiate a radio frequency signal. The piezoelectric effect, and consequently the magnitude of the radio signals, will vary according to the level of gas pressure, the coating properties, the bonding of the coating to the component, and the component material's condition. Such variations in radio frequency signals may be detected using high-temperature micro-receiving antennas.

Alternatively, gas pressure on the blades will cause the blades to deflect under strain. This will cause an electric current between the thermal barrier coating and the component resulting from an electrostrictive effect. This current will cause the blade or vane to radiate a radio frequency signal. The electrostrictive effect, and consequently the magnitude of the radio signals, will vary according to the level of gas pressure, the coating properties, the bonding of the coating to the component, and the component material's condition. As above, such variations in radio frequency signals may be detected using high-temperature micro-receiving antennas.

As a second alternative, friction between the gas and thermal barrier coating will result in tribo-charging. The result will be static electricity within the coating. This static electricity will cause the blade or vane to radiate a radio frequency signal. The tribo-charging, and consequently the magnitude of the radio signals, will vary according to the level of gas pressure, the coating properties, the bonding of the coating to the component, and the component material's condition. As above, such variations in radio frequency signals may be detected using high-temperature micro-receiving antennas.

Regardless of the specific origin of the electricity created within the coating, the resulting radio frequency signal will encompass a wide range of frequencies. The signals received through the antenna may pass through a filter for filtering out frequency ranges present from other sources at that location, and an amplifier, before proceeding to a storage scope for viewing, and/or a computer for storage and analysis. Determining which blade requires servicing uses a single antenna proximate to one vane, in conjunction with a "marking blade" designed to create a different radio frequency signal than the other blades as it passes the antenna. Such a marking blade may be produced by designing a coating intended to produce a greater piezoelectric effect, for example, by adding piezoelectric materials such as lead zirconate titanate to the coating. A blade requiring service will generate a different magnitude radio frequency signal than the remaining blades. When viewing a sequence of radio frequency signals, the number of signals between the marking blade and the blade generating a different magnitude signal can be used to determine the blade requiring service.

If monitoring of the coating on the vanes is also desired, an antenna corresponding to each vane may be used. A blade passing a vane will cause increased gas pressure on both the blade and the vane, resulting in each having a piezoelectric effect and each therefore giving off a radio frequency signal. The piezoelectric effect and resulting radio frequency signal within each vane is likely to be different from that within a blade, and can therefore be distinguished from the blade's signal. Alternatively, a longer antenna extending adjacent to all vanes in a given row may be used.

It is therefore an aspect of the present invention to provide an apparatus for monitoring the condition of a thermal barrier coating within a combustion turbine while that turbine is operating.

It is another aspect of the present invention to provide a method of monitoring the condition of a thermal barrier coating within a combustion turbine while that turbine is operating.

It is a further aspect of the present invention to create electricity within the thermal barrier coating through a piezoelectric effect, electrostrictive effect, or tribo-charging.

It is another aspect of the present invention to create a radio frequency signal through electricity within the thermal barrier coating, with variations in the characteristics of the radio frequency signal varying according to the condition of the coating.

It is a further aspect of the present invention to provide a high temperature radio frequency antenna for receiving radio frequency signals generated within the thermal barrier coating.

It is another object of the present invention to provide a marking blade producing a different radio frequency signal than the other blades within a combustion turbine.

It is a further object of the present invention to analyze radio frequency signals received from the thermal barrier coating of the various vanes and blades, searching for a signal having a different magnitude or frequency than the remaining signals, indicating a blade or vane requiring service.

A better understanding of the present invention can be obtained from the following description, with reference to the drawings.

BRIEF DESCRIPTION OF THE DRAWINGS

Like reference numbers denote like elements throughout the drawings.

DESCRIPTION OF THE PREFERRED EMBODIMENTS

The preferred embodiment of the invention is a system for online monitoring of the condition of components within a combustion turbine. The invention is particularly useful for monitoring the condition of the thermal barrier coating covering vanes and blades within the turbine. The significance and functioning of the present invention are best understood through a description of the environment within a combustion turbine.

Figure 1:
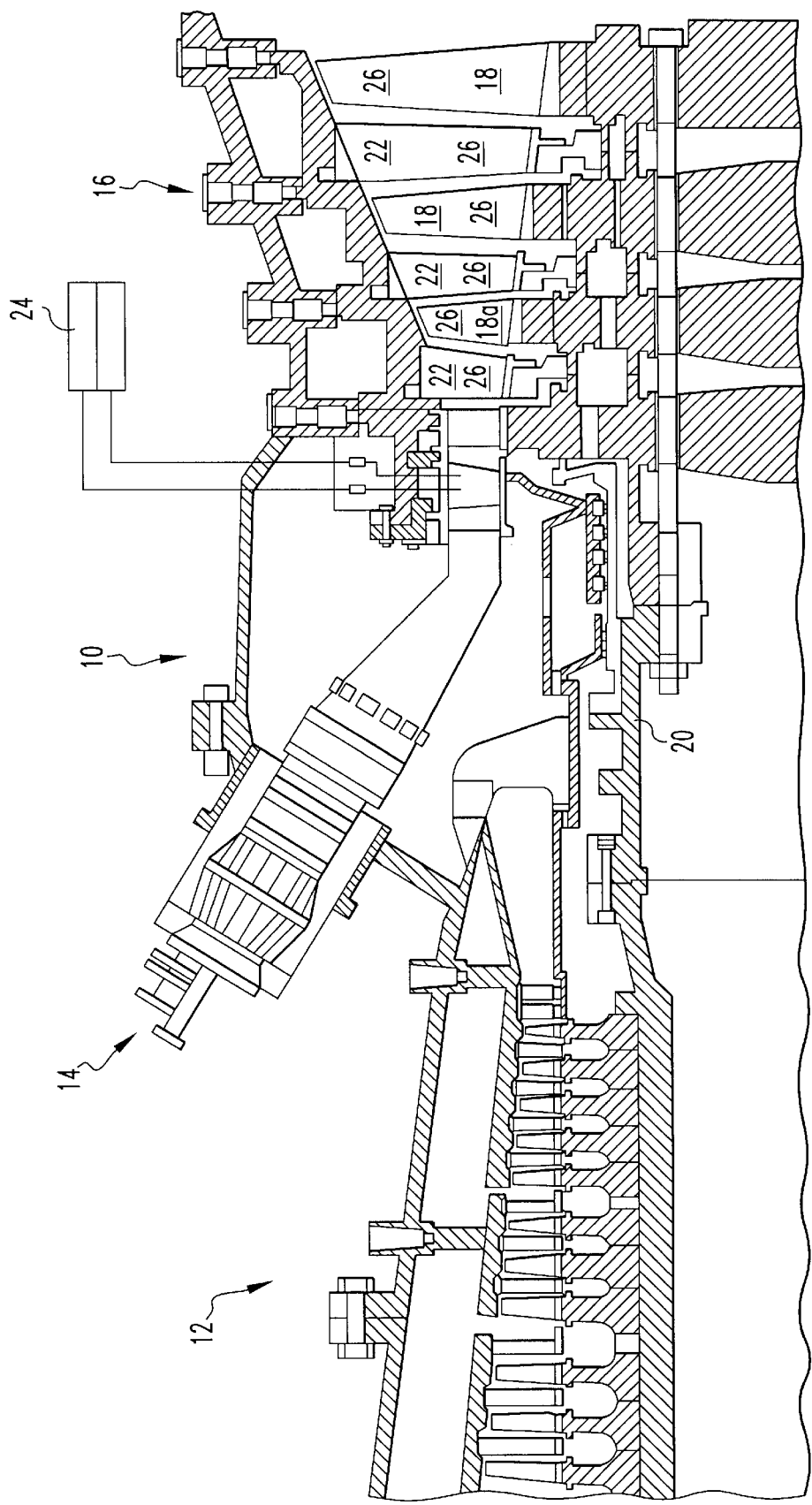
FIG. 1 is a cross sectional view of a combustion turbine for which the present invention will be used.

FIG. 1 illustrates a combustion turbine 10. The combustion turbine 10 includes a compressor 12, at least one combustor 14, and a turbine 16. The turbine 16 includes a plurality of rotating blades 18, secured to a rotatable central shaft 20. A plurality of stationary vanes 22 are positioned between the blades 18, with the vanes 22 being dimensioned and configured to guide air over the blades 18. The blades 18 and vanes will typically be made from nickel-cobalt, and will typically be coated with a thermal barrier coating 26, such as yttria-zirconia.

In use, air is drawn in through the compressor 12, where it is compressed and driven towards the combustor 14. The combustor 14 mixes the air with fuel and ignites it, thereby forming a working gas. This working gas will typically be approximately 2500° F. to 2900° F. (1371° C. to 1593° C.). This gas expands through the turbine 16, being guided across the blades 18 by the vanes 22. As the gas passes through the turbine 16, it rotates the blades 18 and shaft 20, thereby transmitting usable mechanical work through the shaft 20. The combustion turbine 10 also includes a cooling system 24, dimensioned and configured to supply a coolant, for example steam or compressed air, to the blades 18 and vanes 22.

From the above description, it becomes apparent that the environment wherein the vanes 22 and blades 24 operate is particularly harsh, resulting in serious deterioration of the blades 18 and vanes 22 if the thermal barrier coating 26 should deteriorate.

Figure 2:
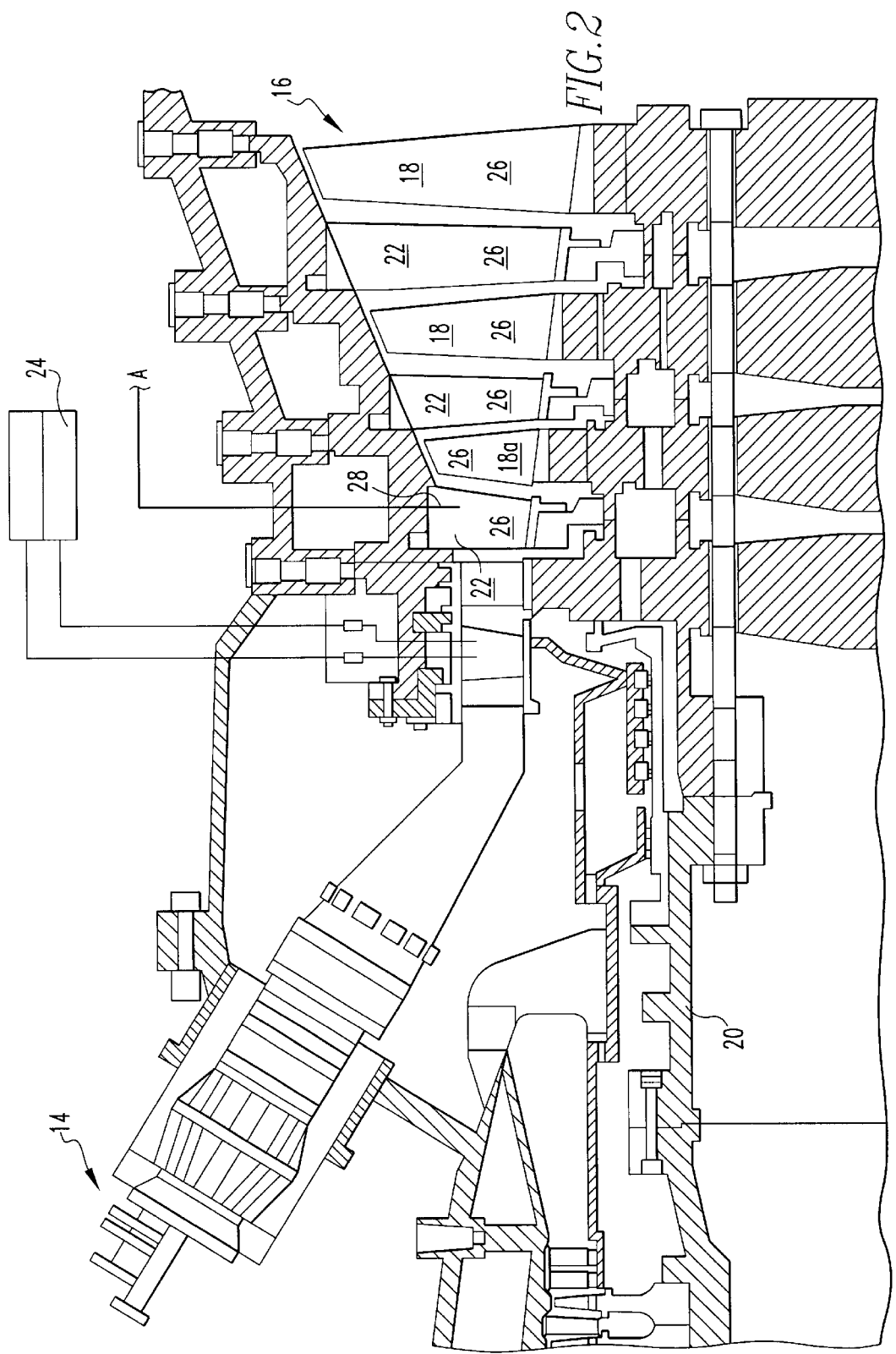
FIG. 2 is a cross sectional view of the turbine portion of a combustion turbine, illustrating the placement of the radio frequency antennas within the turbine, according to the present invention.

Referring to FIG. 2, a high temperature radio frequency antenna 28 is illustrated adjacent to a vane 22. The radio frequency antenna 28 is preferably in close proximity to, but does not touch, the vane 22. Although only one antenna 28 is illustrated, it may be advantageous to use more than one antenna, depending on the monitoring desired. A single antenna 28 will be sufficient if monitoring only the blades 18 in a single row is desired, while multiple antennas 28 may be used if monitoring both blades 18 and vanes 22 in a given row is desired. The blades 18 and vanes 22 in a given row define a single turbine stage. Alternatively, antenna 28 may be elongated to extend past a plurality of vanes, for example, all vanes within a given row. One of such elongated antennas may be provided for each stage. Preferred antennas 28 include a ferrite rod surrounded by a nickel wire, or an antenna made from cobalt. Another alternative is a direct wire connection to the components, with one connection to the coating 26 and another connection to the substrate portion of vane 22.

Figure 3:
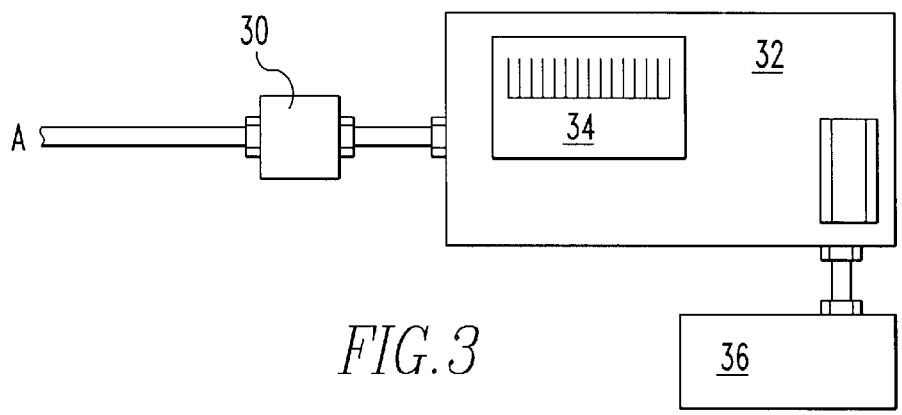
FIG. 3 is a schematic diagram of the apparatus used to analyze and store the radio frequency signals received from a radio frequency antenna, according to the present invention.

Referring to FIGS. 2–3, antenna 28 is electrically connected through electrical lead 29 to an amplifier, filter, and signal conditioner 30, for converting the resonant signal to a sharp spike that is more easily measured and analyzed. The filter 30 is in turn electrically connected to a storage scope 32 having screen 34, for measuring and recording the radio frequency signal, and/or computer 36 for analyzing the radio frequency signals received.

As the turbine is operating, gas pressure on the vanes and blades will apply pressure to the blades 18, vanes 22, and therefore to coating 26. This pressure is capable of causing a piezoelectric effect between the coating 26 and blades 18 or vanes 22. Presently, materials for which a piezoelectric effect are desired are first prepared through polarization. Polarization is accomplished by first heating the material to a high temperature known as the Curie temperature, and then passing DC current through the material. However, the present inventors have discovered that thermal barrier coatings exhibit piezoelectric properties due to the polarization of molecular impurities within the coating, even without the application of electric fields. Therefore, no preparation of the coating is required for the coating to produce a piezoelectric effect.

Alternatively, the pressure will cause a strain within the blades 18, vanes 22, and coating 26, thereby creating an electrostrictive effect between the coating 26 and blades 18 or vanes 22. The resulting current will cause a radio frequency signal to be produced. As a second alternative, friction between the gas and the coating 26 will cause tribo-charging within the coating, resulting in a radio frequency signal caused by the static electricity within the coating 26. The magnitude of the radio signals will vary according to the level of gas pressure, the coating properties, the bonding of the coating 26 to the component, and the component material's condition. Preferably, one blade 18a is dimensioned and configured to produce a different radio frequency signal than the remaining blades 18 and vanes 22. This unique blade thereby becomes a marking blade, whose purpose will be explained below. These radio frequency signals will be detected by the antenna 28.

The antenna 28 will transmit the detected signals to the amplifier and filter 30, which will amplify the signals from the vanes 22 and blades 18, while filtering out signals from other sources, which would have frequencies and magnitudes unlike the desired signals. The radio frequency signals produced by the coating 26 will likely encompass a broad range of frequencies from below radio frequencies to microwaves and beyond, and any subset of these frequencies may be selected for analysis. For example, if the combustion turbine 10 is located in close proximity to another source of radio frequency signals, the filter 30 will preferably be selected to filter out radio frequencies within the range generated by the outside source of signals, thereby leaving only signals having frequencies that are created only by the coating 26 in that particular location. The remaining signals may then be viewed using the storage scope 32, and stored using the computer 36.

Figure 4:
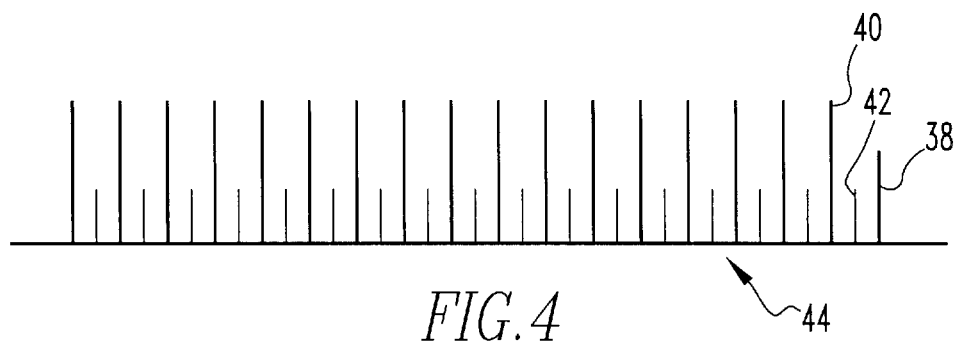
FIG. 4 is a schematic diagram of a radio frequency signal pattern generated by the present invention, denoting an intact blade coating.
Figure 5:
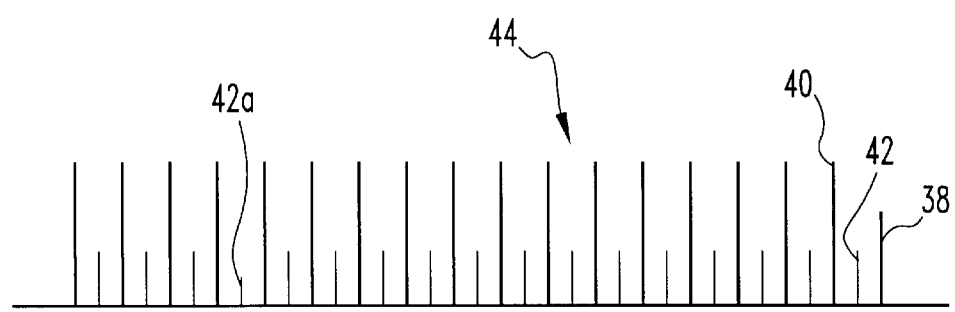
FIG. 5 is a schematic diagram of a radio frequency signal pattern generated by the present invention, denoting a deteriorating blade coating.

Analysis of the signals received is best explained by referring to FIGS. 4–5. These figures illustrate the radio frequency signal patterns 44 detected by a single antenna 28, used to monitor the blades only. The marking blade 18a produces a first radio frequency signal 38. The coating 26 of the marking blade 18a has preferably been prepared to produce a greater piezoelectric effect than the coating 26 on the remaining components of the turbine 16. A preferred way of preparing the marking blade is to include a piezoelectric material with the coating 26, with examples including lead zircanate titanate, barium titanate, and strontium titanate. Alternatively, piezoelectric materials could be added to the coating 26 of all vanes 22 and blades 18, with greater quantities of piezoelectric material added to the marking blade 18a. The vane 22 adjacent to antenna 28 produces a second radio frequency signal 40, differing in magnitude and/or frequency from the first radio signal 38. The remaining blades 18 produce a third radio frequency signal 42, differing in magnitude and/or frequency from the first radio frequency signal 38 and second radio frequency signal 40. FIG. 4 illustrates the pattern of radio frequency signals that will result from all blades having an intact coating. As each blade 18 passes the vane 22 adjacent to antenna 28, the antenna 28 will detect the second radio frequency signal 40 from the vane, and the third radio frequency signal 42 from the blade. The radio frequency signals 42 will have substantially equal magnitudes and frequencies if the coating 26 is intact. Conversely, FIG. 5 illustrates a radio frequency signal pattern indicating a blade 18 having a deteriorating coating 26, as indicated by radio frequency signal 42a, having a lower magnitude than the other radio frequency signals 42. The specific blade 18 producing the signal 42a can be determined by counting the number of signals 42 between the signal 38 of the marking blade 18a to the signal 42a. In the illustrated situation, the blade requiring service is the blade 18 located where it will produce the $14^{th}$ signal from the marking blade's signal 38.

If monitoring both blades 18 and vanes 22 is desired, a separate antenna 26 may be placed adjacent to each vane 22. The above monitoring and analysis is then performed for each individual vane 22. Because each signal pattern 44 will include data from only one vane 22, the signal 40 from that vane is likely to appear substantially constant within a single signal pattern 44, even if the coating 26 is slowly deteriorating. However, comparing the signals 40 from one signal pattern 44 to the signals 40 from the remaining signal patterns 44 will more clearly indicate which vanes require attention. Because the signal pattern 44 indicating a defective vane 22 will be produced from a single antenna 28 adjacent to that vane 22, the vane 22 requiring service is readily identified.

Alternatively, a long antenna 28, passing adjacent to several vanes 22, may be used. Such an antenna 28 will provide signals 40 from multiple vanes 22 within a single signal pattern 40. As above, comparing the signal 40 from one vane 22 to the signals 40 from other vanes 22 will indicate the vane 22 requiring service.

One method of locating components requiring service within the turbine 16 is by using pattern-recognition software to analyze the radio frequency signal information sent to the computer 36, thereby performing the above-described analysis automatically, or at desired time intervals.

While a specific embodiment of the invention has been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

We claim:

1. An apparatus for monitoring the condition of a thermal barrier coating for a substrate, the thermal barrier coating producing electricity within said thermal barrier coating, or between said thermal barrier coating and said substrate, through a means selected from the group consisting of piezoelectric, electrostrictive, and tribo-charging when subjected to an operating environment of the substrate, said apparatus comprising:
   at least one radio frequency antenna dimensioned and configured for placement in close proximity to said thermal barrier coating; and
   means for analyzing a radio frequency signal produced by said electricity and received by said radio frequency antenna to determine the condition of the thermal barrier coating, said radio frequency signal having a magnitude and a frequency.

2. The apparatus according to claim 1, further comprising a plurality of radio frequency antennas.

3. The apparatus according to claim 1, further comprising an elongated radio frequency antenna.

4. The apparatus according to claim 1, wherein said means for analyzing the radio frequency signal include a storage scope for storing the magnitude and frequency of the radio frequency signal.

5. The apparatus according to claim 1, wherein said means for analyzing the radio frequency signal includes a computer for detecting changes in the magnitude and frequency of the radio frequency signal.

6. An apparatus for monitoring the condition of vanes and blades within a combustion turbine, the vanes and blades having a thermal barrier coating, the thermal barrier coating producing electricity within said thermal barrier coating, or between said thermal barrier coating and said substrate, through a means selected from the group consisting of piezoelectric, electrostrictive, and tribo-charging when exposed to an operating environment within the combustion turbine, said apparatus comprising:
   a radio frequency antenna dimensioned and configured for placement in close proximity with one of said vanes within the turbine portion of the combustion turbine; and
   means for analyzing a radio frequency signal produced by said electricity and received by said radio frequency antenna, said radio frequency signal having a magnitude and a frequency.

7. The apparatus according to claim 6, further comprising a plurality of radio frequency antennas, each of said radio frequency antennas being dimensioned and configured for placement in close proximity with one of said vanes.

8. The apparatus according to claim 6, further comprising an elongated radio frequency antenna dimensioned and configured for placement in close proximity to a plurality of said vanes.

9. The apparatus according to claim 6, wherein said means for analyzing the radio frequency signal include a storage scope for storing the magnitude and frequency of the radio frequency signal.

10. The apparatus according to claim 6, wherein said means for analyzing the radio frequency signal includes a computer for monitoring the magnitude and frequency of the radio frequency signal.

11. An apparatus for monitoring the condition of vanes and blades within a combustion turbine, the vanes and blades having a thermal barrier coating, the thermal barrier coating producing electricity through a means selected from the group consisting of piezoelectric, electrostrictive, and tribo-charging when exposed to an operating environment within the combustion turbine, said apparatus comprising:
   a radio frequency antenna dimensioned and configured for placement in close proximity with one of said vanes within the turbine portion of the combustion turbine;
   means for analyzing a radio frequency signal produced by said electricity and received by said radio frequency antenna, said radio frequency signal having a magnitude and a frequency; and
   a marker blade within the combustion turbine, said marker blade producing a first radio frequency signal, said vanes producing a second radio frequency signal, and said blades producing a third radio frequency signal.

12. The apparatus according to claim 11, wherein said thermal barrier coating of said marker blade includes a piezoelectric material.

13. The apparatus according to claim 11, wherein said means for analyzing the radio frequency signal includes:
   means for identifying a radio frequency signal differing from said first radio frequency signal, said second radio frequency signal, and said third radio frequency signal; and
   means for counting from said marking blade to said radio frequency signal differing from said first radio frequency signal, said second radio frequency signal, and said third radio frequency signal, thereby identifying the component requiring inspection.

14. A combustion turbine, comprising:
   a plurality of blades;
   a plurality of vanes;
   a thermal barrier coating covering said blades and said vanes the thermal barrier coating being adapted for production of electricity through a means selected from the group consisting of piezoelectric, electrostrictive, and tribo-charging;
   a radio frequency antenna dimensioned and configured for placement within the turbine portion of the combustion turbine; and
   means for analyzing a radio frequency signal produced by said electricity and received by said radio frequency antenna, said radio frequency signal having a magnitude and a frequency.

15. The apparatus according to claim 14, further comprising a plurality of radio frequency antennas, each of said radio frequency antennas being dimensioned and configured for placement in close proximity with one of said vanes.

16. The apparatus according to claim 14, further comprising an elongated radio frequency antenna dimensioned and configured for placement in close proximity to a plurality of said vanes.

17. The apparatus according to claim 14, wherein said means for analyzing the radio frequency signal include a storage scope for storing the magnitude and frequency of the radio frequency signal.

18. The apparatus according to claim 14, wherein said means for analyzing the radio frequency signal includes a computer for monitoring the magnitude and frequency of the radio frequency signal.

19. The apparatus according to claim 14, further comprising a marker blade within the combustion turbine, said marker blade producing a first radio frequency signal, said vanes producing a second radio frequency signal, and said blades producing a third radio frequency signal.

20. The apparatus according to claim 19, wherein said thermal barrier coating of said marker blade includes a piezoelectric material.

21. The apparatus according to claim 19, wherein said means for analyzing the radio frequency signal includes:

means for identifying a radio frequency signal differing from said first radio frequency signal, said second radio frequency signal, and said third radio frequency signal; and means for counting from said first radio frequency signal to said radio frequency signal differing from said first radio frequency signal, said second radio frequency signal, and said third radio frequency signal, thereby identifying the component requiring inspection.

22. A method of monitoring the condition of a thermal barrier coating for a substrate, said method comprising:

applying a pressure to said coating, creating electricity between said coating and said substrate;

said electricity generating a radio frequency signal having a magnitude and a frequency;

receiving said radio frequency signal; and analyzing said radio frequency signal to determine if a defect exists in the thermal barrier coating.

23. The method according to claim 22, wherein said pressure causes a piezoelectric effect between said coating and said substrate.

24. The method according to claim 22, wherein said pressure causes a strain within said substrate, thereby causing an electrostrictive effect between said substrate and said coating.

25. The method according to claim 22, wherein said pressure is applied by a gas, resulting in a friction between the gas and said coating, thereby causing tribo-charging within said coating.

26. The method according to claim 22, wherein:

said radio frequency signal has a magnitude and frequency; and said step of analyzing said radio frequency signal includes the step of storing said magnitude and frequency of said signal.

27. The method according to claim 26, wherein said step of analyzing said radio frequency signal includes the step of looking for changes in said magnitude and/or said frequency of said signal.

28. The method according to claim 26, wherein:

a plurality of radio frequency signals are received; and said step of analyzing said radio frequency signal includes the step of comparing said plurality of radio frequency signals for changes in magnitude and/or frequency.

29. The method according to claim 22, wherein said thermal barrier coating is applied to components of a combustion turbine, said components being selected from the group consisting of vanes and blades.

30. A method of monitoring the condition of a thermal barrier coating for a substrate, said method comprising:

providing components within a combustion turbine, said components being selected from the group consisting of vanes and blades, said vanes and blades having said thermal barrier coating applied to them;

providing a marking blade within said combustion turbine;

applying a pressure to said coating, creating an electric current flowing between said coating and said substrate;

said current generating a radio frequency signal having a magnitude and a frequency;

said marking blade being dimensioned and configured to produce a radio frequency signal different from said signals produced by said other blades and vanes;

receiving said radio frequency signal; and analyzing said radio frequency signal to determine if a defect exists in the thermal barrier coating.

31. The method according to claim 30, wherein said step of analyzing said radio frequency signal comprises the steps of:

receiving sequentially a series of radio frequency signals received from a plurality of components selected from the group consisting of vanes and blades, said vanes producing a second radio frequency signal, said blades producing a third radio frequency signal;

identifying any radio frequency signal having a magnitude substantially unequal to said first radio frequency signal, said second radio frequency signal, and said third radio frequency signal; and counting from said radio signal identifying said marking blade to said radio frequency signal unequal to said first radio frequency signal, said second radio frequency signal, and said third radio frequency signal, thereby identifying the component requiring inspection.

* * * * *